United States Patent
Andreacchi et al.

(10) Patent No.: US 9,662,677 B2
(45) Date of Patent: May 30, 2017

(54) DRUG-COATED BALLOON WITH LOCATION-SPECIFIC PLASMA TREATMENT

(75) Inventors: Anthony S. Andreacchi, San Jose, CA (US); Stephen D. Pacetti, San Jose, CA (US); John Stankus, Campbell, CA (US); Victoria M. Gong, Sunnyvale, CA (US); Michael J. Leonard, Palo Alto, CA (US); Binh Nguyen, Newark, CA (US)

(73) Assignee: ABBOTT LABORATORIES, Santa Clara, CA (US)

( * ) Notice: Subject to any disclaimer, the term of this patent is extended or adjusted under 35 U.S.C. 154(b) by 864 days.

(21) Appl. No.: 12/883,024

(22) Filed: Sep. 15, 2010

(65) Prior Publication Data

US 2012/0064141 A1  Mar. 15, 2012

(51) Int. Cl.
| | |
|---|---|
| *B05D 3/06* | (2006.01) |
| *C23C 14/02* | (2006.01) |
| *A61F 2/00* | (2006.01) |
| *B05D 3/14* | (2006.01) |
| *B05D 7/02* | (2006.01) |
| *C08J 7/12* | (2006.01) |
| *A61F 2/82* | (2013.01) |

(52) U.S. Cl.
CPC ............... *B05D 3/144* (2013.01); *B05D 7/02* (2013.01); *C08J 7/123* (2013.01); *A61F 2/82* (2013.01)

(58) Field of Classification Search
CPC .. C05D 3/06; A61F 2/00; C23C 14/02; B05D 3/06

USPC .......................................................... 427/2.1
See application file for complete search history.

(56) References Cited

U.S. PATENT DOCUMENTS

| | | |
|---|---|---|
| 4,748,982 A | 6/1988 | Horzewski et al. |
| 4,963,313 A | 10/1990 | Noddin et al. |
| 5,300,085 A | 4/1994 | Yock |
| 5,324,261 A * | 6/1994 | Amundson ............. A61F 2/958 604/103.02 |
| 5,370,614 A | 12/1994 | Amundson et al. |
| 5,464,650 A | 11/1995 | Berg et al. |
| 5,496,346 A | 3/1996 | Horzewski et al. |
| 5,591,227 A | 1/1997 | Dinh et al. |
| 5,626,600 A | 5/1997 | Horzewski et al. |

(Continued)

OTHER PUBLICATIONS

Bhat, G.K., "Potential, problems and innovations of plasma heat applications in the metallurgical industry," *Pure & Appl. Chem.*, 1984, 56(2): 209-214.

(Continued)

*Primary Examiner* — Binu Thomas
*Assistant Examiner* — Hai Yan Zhang
(74) *Attorney, Agent, or Firm* — Baker Botts L.L.P.

(57) ABSTRACT

Method of coating an expandable member, e.g. balloon, is provided, the method comprising providing an expandable member having an outer surface. The method includes a plasma treatment with a supply of gas performed on at least a portion of the outer surface of the expandable member. A therapeutic agent is applied on at least the plasma treated portion of the outer surface of the expandable member after the plasma treatment is performed. The plasma treatment can reduce the adhesion of therapeutic agent to the surface of the expandable member. A medical device made by the disclosed method is also provided.

43 Claims, 12 Drawing Sheets

(56) References Cited

U.S. PATENT DOCUMENTS

| | | | |
|---|---|---|---|
| 5,649,977 | A | 7/1997 | Campbell |
| 5,714,110 | A | 2/1998 | Wang et al. |
| 5,879,697 | A * | 3/1999 | Ding ..................... A61L 27/34 424/422 |
| 5,911,452 | A | 6/1999 | Yan |
| 6,120,364 | A | 9/2000 | Laflamme |
| 6,358,556 | B1 | 3/2002 | Ding et al. |
| 6,361,819 | B1 * | 3/2002 | Tedeschi et al. ............ 427/2.24 |
| 6,406,457 | B1 | 6/2002 | Wang et al. |
| 6,478,807 | B1 | 11/2002 | Foreman et al. |
| 6,494,906 | B1 | 12/2002 | Owens |
| 6,610,068 | B1 * | 8/2003 | Yang ..................... A61F 2/958 606/108 |
| 6,669,980 | B2 | 12/2003 | Hansen |
| 6,849,306 | B2 | 2/2005 | Fukuda et al. |
| 6,954,977 | B2 * | 10/2005 | Maguire et al. ............... 29/460 |
| 6,988,881 | B2 | 1/2006 | Motsenbocker et al. |
| 7,144,606 | B2 | 12/2006 | Huang |
| 7,192,395 | B1 * | 3/2007 | Qu et al. ......................... 600/1 |
| 7,241,344 | B2 | 7/2007 | Worsham et al. |
| 7,335,227 | B2 | 2/2008 | Jalisi |
| 7,378,105 | B2 | 5/2008 | Burke et al. |
| 7,445,792 | B2 | 11/2008 | Toner et al. |
| 7,455,876 | B2 | 11/2008 | Castro et al. |
| 8,778,014 | B1 * | 7/2014 | Dugan ..................... A61F 2/86 623/1.46 |
| 2002/0123788 | A1 * | 9/2002 | Sanders Millare ....... A61F 2/07 623/1.13 |
| 2004/0127425 | A1 * | 7/2004 | Nudler ................. A61K 9/0014 514/1.4 |
| 2004/0234748 | A1 | 11/2004 | Stenzel |
| 2005/0107870 | A1 * | 5/2005 | Wang et al. ................. 623/1.44 |
| 2007/0088255 | A1 | 4/2007 | Toner et al. |
| 2008/0002146 | A1 * | 1/2008 | Stachowski et al. ..... 351/160 H |
| 2009/0123516 | A1 * | 5/2009 | Agrawal et al. .............. 424/423 |
| 2010/0023108 | A1 | 1/2010 | Toner et al. |
| 2010/0030183 | A1 | 2/2010 | Toner et al. |
| 2010/0055294 | A1 | 3/2010 | Wang et al. |
| 2010/0087783 | A1 * | 4/2010 | Weber et al. ............ 604/103.02 |
| 2010/0233228 | A1 * | 9/2010 | Speck ........................... 424/422 |
| 2011/0301299 | A1 * | 12/2011 | Chen ..................... A61L 27/16 525/326.4 |

OTHER PUBLICATIONS

Schütze, et al., "The atmospheric-pressure plasma jet: A review and comparison to other plasma sources," *IEEE Transactions on Plasma Science*, Dec. 1998, 26(6): 1685-1694.

Stöhr, et al., "Multilayer photoresist stamps for selective plasma treatment in micrometer scales," *Plasma Processes and Polymers*, 2009, vol. 6: 228-233.

Stöhr, et al., "Porous photoresist stamps for selective plasma treatment," *Plasma Processes and Polymers*, 2010, vol. 7: 9-15.

Unverdoben, Martin, "The Paclitaxel-Eluting PTCA-Balloon Catheter in Coronary Artery Disease PEPCAD I-SVD PEPCAD II-ISR," Clinical Research Institute, Center for Cardiovascular Diseases, 2005-2006, Rotenberg, Germany.

* cited by examiner

A-A

B-B

| Sorted Parameter Estimates | | | | | | |
|---|---|---|---|---|---|---|
| Argon—no hold Term | Estimate | Std Error | t Ratio | | | Prob>|t| |
| Time (s)(40,420) | −3.1675 | 3.175281 | −1.00 | | | 0.4236 |
| Power (W)(62,700) | −0.2775 | 3.175281 | −0.09 | | | 0.9383 |

| Sorted Parameter Estimates | | | | | | |
|---|---|---|---|---|---|---|
| Argon—hold Term | Estimate | Std Error | t Ratio | | | Prob>|t| |
| Time (s)(40,420) | −5.4175 | 2.724267 | −1.99 | | | 0.1851 |
| Power (W)(62,700) | 2.8075 | 2.724267 | 1.03 | | | 0.4111 |

| Sorted Parameter Estimates | | | | | | |
|---|---|---|---|---|---|---|
| Oxygen/Argon Term | Estimate | Std Error | t Ratio | | | Prob>|t| |
| Time (s)(40,420) | 11.1125 | 1.649028 | 6.74 | | | (0.0213*) |
| Power (W)(62,700) | −1.4025 | 1.649028 | −0.85 | | | 0.4846 |

Argon-no hold

| Sorted Parameter Estimates | | | | | |
|---|---|---|---|---|---|
| Term | Estimate | Std Error | t Ratio | | Prob>\|t\| |
| Power (W)(62,700) | -1.61 | 0.720014 | -2.24 | | 0.2677 |
| Time (s)(40,420) | -0.41 | 0.720014 | -0.57 | | 0.6705 |
| Power (W)*Time (s) | 0.41 | 0.720014 | 0.57 | | 0.6705 |

Argon-hold

| Sorted Parameter Estimates | | | | | |
|---|---|---|---|---|---|
| Term | Estimate | Std Error | t Ratio | | Prob>\|t\| |
| Time (s)(40,420) | -2.06 | 0.675293 | -3.05 | | 0.2017 |
| Power (W)(62,700) | 1.365 | 0.675293 | 2.02 | | 0.2925 |
| Power (W)*Time (s) | -1.235 | 0.675293 | -1.83 | | 0.3186 |

Oxygen/Argon

| Sorted Parameter Estimates | | | | | |
|---|---|---|---|---|---|
| Term | Estimate | Std Error | t Ratio | | Prob>\|t\| |
| Time (s)(40,420) | 6.9075 | 2.677691 | 2.58 | | 0.2354 |
| Power (W)*Time (s) | 3.8875 | 2.677691 | 1.45 | | 0.3840 |
| Power (W)(62,700) | -1.6775 | 2.677691 | -0.63 | | 0.6437 |

Figure 9

DRUG-COATED BALLOON WITH LOCATION-SPECIFIC PLASMA TREATMENT

BACKGROUND OF THE DISCLOSED SUBJECT MATTER

Field of the Disclosed Subject Matter

The presently disclosed subject matter is related to the coating of interventional medical devices, and particularly coating of therapeutic agents on an expandable member of a medical device. More particularly, the presently disclosed subject matter relates to a method for performing a plasma treatment to a balloon prior to applying a therapeutic agent on the balloon.

Description of Related Subject Matter

Atherosclerosis is a syndrome affecting arterial blood vessels. It is characterized by a chronic inflammatory response in the walls of arteries, which is in large part due to the accumulation of lipid, macrophages, foam cells and the formation of plaque in the arterial wall. Atherosclerosis is commonly referred to as hardening of the arteries, although the pathophysiology of the disease manifests itself with several different types of lesions ranging from fibrotic to lipid laden to calcified. Angioplasty is a vascular interventional technique involving mechanically widening an obstructed blood vessel, typically caused by atherosclerosis.

During angioplasty, a catheter having a folded balloon is inserted into the vasculature of the patient and is passed to the narrowed location of the blood vessel at which point the balloon is inflated to the desired size by fluid pressure. Percutaneous coronary intervention (PCI), commonly known as coronary angioplasty, is a therapeutic procedure to treat the stenotic regions in the coronary arteries of the heart, often found in coronary heart disease. In contrast, peripheral angioplasty, commonly known as percutaneous transluminal angioplasty (PTA), generally refers to the use of mechanical widening of blood vessels other than the coronary arteries. PTA is most commonly used to treat narrowing of the leg arteries, especially, the iliac, external iliac, superficial femoral and popliteal arteries, and arteries more distal to these in the lower limbs. PTA can also treat narrowing of carotid and renal arteries, veins, and other blood vessels.

Although the blood vessel is often successfully widened by angioplasty, sometimes the treated region of the blood vessel undergoes vasospasm, or abrupt closure after balloon inflation or dilatation, causing the blood vessel to collapse after the balloon is deflated or shortly thereafter. One solution to such collapse is stenting the blood vessel to prevent collapse. Dissection, or perforation, of the blood vessel is another complication of angioplasty, which can be improved by stenting. A stent is a device, typically a metal tube or scaffold that is inserted into the blood vessel after, or concurrently with angioplasty, to hold the blood vessel open.

While the advent of stents eliminated many of the complications of abrupt vessel closure after angioplasty procedures, within about six months of stenting a re-narrowing of the blood vessel can form, a condition known as restenosis. Restenosis was discovered to be a response to the injury of the angioplasty procedure and is characterized by a growth of smooth muscle cells and extracellular matrix—analogous to a scar forming over an injury. To address this condition, drug eluting stents were developed to reduce the reoccurrence of blood vessel narrowing after stent implantation. A drug eluting stent is a stent that has been coated with a drug, often in a polymeric carrier, that is known to interfere with the process of re-narrowing of the blood vessel (restenosis).

Examples of various known drug eluting stents are disclosed in U.S. Pat. Nos. 5,649,977; 5,464,650; 5,591,227, 7,378, 105; 7,445,792; 7,335,227, all of which are hereby incorporated by reference in their entirety. However, a drawback of drug eluting stents is a condition known as late stent thrombosis. This is an event where a blood clot forms inside the stent, which can occlude blood flow.

Drug coated balloons are believed to be a viable alternative to drug eluting stents in the treatment of atherosclerotic lesions. In a study which evaluated restenosis, and the rate of major adverse cardiac events such as heart attack, bypass, repeat stenosis, or death in patients treated with drug coated balloons and drug eluting stents, the patients treated with drug coated balloons experienced only 3.7% restenosis and 4.8% MACE (material adverse coronary events) as compared to patients treated with drug eluting stents, in which restenosis was 20.8 percent and 22.0 percent MACE rate. (See, PEPCAD II study, Rotenburg, Germany).

A drug coated balloon is a unique drug-device combination product. In addition to performing a dilatation function, it must deliver a therapeutic level of drug to the vascular tissue during an inflation that lasts only thirty seconds to a few minutes. This rapid transfer of drug requires coatings that release a large fraction of drug during the balloon inflation. While there are many potential mechanisms of drug transfer for a drug coated balloon, the primary ones are: transfer of coating to the vessel wall with subsequent diffusion of drug into tissue; insertion of coating into tissues or fissures in the vessel wall produced by the dilatation; pressing the coating against the vessel wall, the drug dissolving into a thin liquid film to create a drug saturated boundary layer, and this dissolved drug diffusing into the tissue; and drug dissolving the entire time the balloon is near, or expanded against, the vessel wall and this dissolved drug diffusing into the tissue.

However, drug coated balloons present certain unique challenges. For example, the drug carried by the balloon needs to remain on the balloon during delivery to the lesion site, and released from the balloon surface to the blood vessel wall when the balloon is expanded inside the blood vessel. For coronary procedures, the balloon is typically inflated for less than one minute, typically about thirty seconds. The balloon inflation time can be longer for a peripheral procedure, however typically even for peripheral procedures the balloon is expanded for less than five minutes. Due to the short duration of contact between the drug coated balloon surface and the blood vessel wall, the balloon coating must exhibit efficient therapeutic agent transfer and/or efficient drug release during inflation. Thus, there are challenges specific to drug delivery via a drug coated or drug eluting balloon that are not present with a drug eluting stent.

Furthermore, conventional drug eluting stent coating processes are not desirable for coating balloons. Such conventional techniques include spraying (air-atomization, ultrasonic, electrostatic, etc.), but might also include roll-coating, dip-coating, spin-coating, vapor deposition, micro-droplet coating, etc. Coating adhesion needs to be robust enough to withstand manufacturing processing, for example, balloon refolding in the dry state, and to survive procedural stresses, for example, passage through the hemostatic valve, guide sheath and tracking to the lesion site when wet. However, coating adhesion also needs to be weak enough such that when the balloon is expanded and pressed into the vessel wall, the drug, drug-polymer, or drug-excipient is transferred. For example, if the coating adhesion is too high, a large majority of the drug remains on the balloon and is still present when the balloon is deflated and removed, even after balloon expansion. Accordingly, coating adhesion needs to be tuned to minimize drug loss during delivery and potential toxic effects from systemic drug exposure, and maximize drug release upon balloon expansion.

The balloon material substrate is fixed and chosen largely for its properties as a dilation balloon. The coating properties can be altered by combining the therapeutic agent with various excipients. Coating structure and physical properties are also dependent on the method of application, e.g., spraying, liquid dispensing, dip-coating, roll coating, etc., and by modulating specific coating parameters, e.g., simultaneous coating-drying, in-line drying, post-coating oven cure, etc. However, the properties of the coating are often dominated by those of the therapeutic agent and excipients, e.g., percentage of drug solids, as it comprises a majority of the coating in order to keep the coating from becoming too thick.

Thus, there remains a need for an efficient and economic method and system for tuning coating on medical devices. The disclosed subject matter addresses this need by performing a plasma treatment to the surface of an expandable member of a medical device prior to coating a therapeutic agent to the expandable member.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and medical devices particularly pointed out in the written description and claims thereof, as well as from the appended drawings.

To achieve these and other advantages, and in accordance with the purpose of the disclosed subject matter, as embodied and broadly described, the disclosed subject matter includes a method for assembly of an expandable member having one or more therapeutic agents coated thereon in such a manner that does not result in damage or loss of therapeutic agent, nor contamination of the equipment employed.

In accordance with an aspect of the disclosed subject matter, a method of coating an expandable member is provided. The method includes providing an expandable member having an outer surface. A plasma treatment with a supply of gas is performed on at least a portion of the outer surface of the expandable member. After the plasma treatment is performed, a therapeutic agent is disposed on at least the plasma treated portion of the outer surface of the expandable member.

The plasma treatment can be performed by using a low pressure plasma system. The low pressure plasma system includes a vacuum system. Alternatively, or additionally, the plasma treatment can be performed by using an atmospheric plasma system. The plasma treatment can be performed by various devices in the art, including, but not limited to a plasma jet, a plasma stamp, a plasma plume, a plasma torch, flame plasma, corona discharge, or ozone treatment. The plasma treatment is performed within a plasma reactor chamber.

The plasma treatment is performed by a supply of gas. The gas can include argon, helium, neon, krypton, xenon, radon, nitrogen, ammonia, and a combination thereof. In one embodiment, the gas is argon. The gas can further include oxygen, ozone, hydrogen peroxide, carbon dioxide, carbon monoxide, carbon tetrafluoride, hydrogen, nitrogen, water vapor, nitrogen oxides, ammonia, allyl amine, allyl alcohol, methane, and a combination thereof. In one embodiment, the plasma treatment is performed with a mixture of argon and oxygen. The ratio of argon:oxygen in such mixture is from about 10:90 to about 90:10 by volume. In one embodiment, the ratio of argon:oxygen in such mixture is about 50:50 by volume.

The plasma treatment can be performed at various conditions. Generally, plasma is generated by a plasma frequency of from about 1 kHz to about 2,500 MHz. In various embodiments, the plasma is generated by a plasma frequency of from about 10 kHz to about 14 MHz, or more particularly, from about 40 kHz to about 14 MHz. In one embodiment, the plasma treatment is performed at a power of from about 62 watts to about 700 watts, such as about 380 watts. In one embodiment, the gas flow rate for the plasma treatment is from about 0.9 standard liters per minute to about 1.2 standard liters per minute, such as about 1.08 standard liters per minute. The plasma is generated at a pressure of from about 1 mTorr to about 2,000 mTorr. In one embodiment, the plasma is generated at a pressure of from about 50 mTorr to about 500 mTorr with about 250 mTorr as nominal pressure. Alternatively or additionally, the plasma is generated at an atmospheric pressure. In various embodiments, the plasma is generated at a pressure of from about 680 Torr to about 1,520 Torr, from about 720 Torr to about 800 Torr, or about 760 Torr. The plasma treatment is performed at a temperature of from about 16 degrees Celsius (° C.) to about 100° C. In one embodiment, the plasma treatment is performed at a temperature of from about 25° C. to about 45° C. The expandable member is exposed to the plasma treatment for from about 10 seconds to about 1,000 seconds. In one embodiment, the expandable member is exposed to the plasma treatment for from about 40 seconds to about 420 seconds, such as at least about 75 seconds. In one embodiment, the expandable member is exposed to the supplied gas for about 15 minutes or less after the plasma treatment is complete.

The therapeutic agent can be applied by spraying, dipping, syringe coating, electrospinning, electrostatic coating, direct coating, roll coating, or a combination thereof. The therapeutic agent can be selected from the group consisting of zotarolimus, everolimus, rapamycin, biolimus, myolimus, novolimus, deforolimus, temsirolimus, paclitaxel, protaxel, or a combination thereof although other therapeutic agents are contemplated, including but not limited to the steroids dexamethasone, dexamethasone acetate, clobetisol, etc. The therapeutic agent can further comprise at least one compound selected from the group consisting of excipients, binding agents, plasticizers, solvents, surfactants, additives, chelators, or fillers. The excipient can be selected from the group consisting of contrast agents, polysaccharides, amino acids, proteins, non-ionic hydrophilic polymers, ionic hydrophilic polymers, acrylates, hydrophobic polymers, aliphatic polyesters and polyester block copolymers, and mucoadhesives. In one embodiment, the excipient is polyvinylpyrrolidone. In one embodiment, the plasticizer is glycerol.

The expandable member can be composed of nylon 12, nylon 11, nylon 9, nylon 6, nylon 6/12, nylon 6/11, nylon 6/9, nylon 6/6, PEBAX® nylon polyether copolymer, blends of PEBAX® and nylon, HYTREL®, polyethylene, or a combination thereof.

In accordance with another aspect of the invention, performing the plasma treatment with a supply of gas on at least a portion of the outer surface of the expandable member includes covering a select portion of the outer surface of the expandable member with a covering member. A plasma treatment is performed with a supply of gas on the outer surface of the expandable member, which is covered by the covering member. The covering member can be removed after the plasma treatment is completed. The covering member can be made of silicone, polyethylene (PE), low density polyethylene (LDPE), very low density polyethylene (VLDPE), high density polyethylene (HDPE), ultra high molecular weight polyethylene (UHMWPE), poly(tetrafluoroethylene) (PTFE) (also referred as "Teflon®"), fluorinated ethylene propylene (FEP), polyether ether ketone (PEEK), aluminum, stainless steel, or combinations thereof.

In one embodiment, the expandable member is in a folded configuration before performing the plasma treatment. The method further includes inflating the expandable member with a select amount of inflation medium before performing the plasma treatment. In another embodiment, the expandable member is in an expanded configuration before performing the plasma treatment.

The method can further include deflating the expandable member to impart a plurality of folds therein after performing the plasma treatment. The fold has an inside portion and an outside portion. In one embodiment, after deflating the expandable member, the method can further include folding the expandable member, which results in the plasma treated portion of the expandable being the inside portions of the folds.

In accordance with another aspect of the disclosed subject matter, a coating of a therapeutic agent can be applied to an outer surface of an expandable member of a medical device by performing a plasma treatment with a supply of gas on at least a portion of the outer surface, and applying a therapeutic agent on at least the plasma treated portion of the outer surface after performing the plasma treatment.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

FIG. 9 is a graphical representation of results from in vitro "Just in With Expansion" assay from Example 2.

DETAILED DESCRIPTION OF THE PREFERRED EMBODIMENT

Reference will now be made in detail to the preferred embodiments of the disclosed subject matter, an example of which is illustrated in the accompanying drawing. The method and corresponding steps of the disclosed subject matter will be described in conjunction with the detailed description of the system.

Unless otherwise defined, all technical and scientific terms used herein have the same meanings as commonly understood by one of ordinary skill in the art to which the disclosed subject matter belongs. Although methods and materials similar or equivalent to those described herein can be used in its practice, suitable methods and materials are described below It is to be noted that the term "a" entity or "an" entity refers to one or more of that entity. As such, the terms "a", "an", "one or more", and "at least one" can be used interchangeably herein. The terms "comprising," "including," and "having" can also be used interchangeably. In addition, the terms "amount" and "level" are also interchangeable and can be used to describe a concentration or a specific quantity. Furthermore, the term "selected from the group consisting of" refers to one or more members of the group in the list that follows, including mixtures (i.e. combinations) of two or more members.

The term "about" means within an acceptable error range for the particular value as determined by one of ordinary skill in the art, which will depend in part on how the value is measured or determined, i.e., the limitations of the measurement system.

The methods and systems presented herein can be used for manufacture and assembly of medical devices such as a drug coated balloon catheter. The disclosed subject matter is particularly suited for tuning adhesion of a coating of therapeutic agent to an expandable member of a medical device. While the disclosed subject matter references application of a therapeutic agent, it is to be understood that a variety of coatings including polymeric, therapeutic, or matrix coatings, can be applied to various surfaces of medical devices, as so desired.

In accordance with the disclosed subject matter, a method of coating an expandable member is provided. The method includes providing an expandable member having an outer surface. A plasma treatment is performed with a supply of gas on at least a portion of the outer surface of the expandable member. After the plasma treatment is performed, a therapeutic agent is disposed on at least the plasma treated portion of the outer surface of the expandable member.

Figure 1:
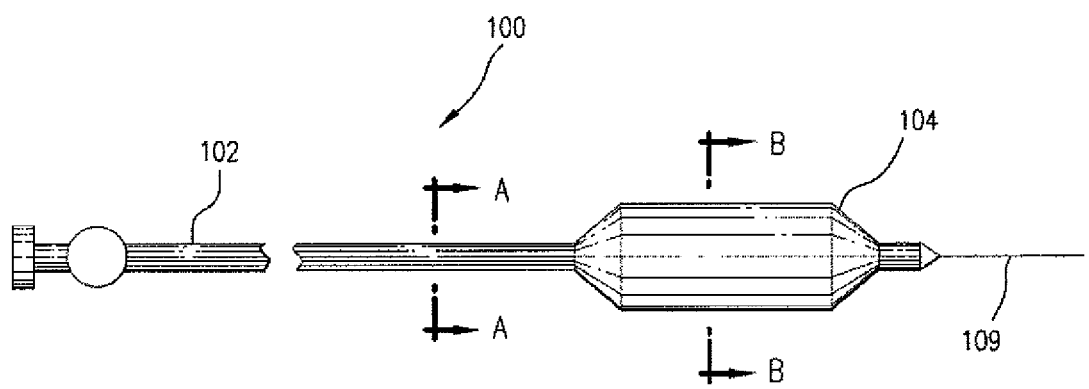
FIG. 1 is a side view of a catheter having an expandable member in accordance with the invention.
Figure 2:
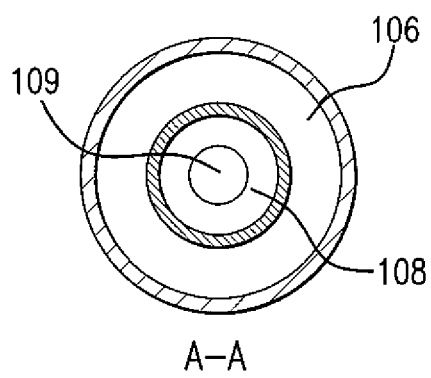
FIG. 2 is a cross-sectional view taken along lines A-A in FIG. 1 in accordance with one embodiment of the invention.

For purpose of explanation and illustration, and not limitation, an exemplary embodiment of a medical device having an expandable member is shown schematically in FIGS. 1 and 2. As shown in FIGS. 1 and 2, the medical device 100 generally includes an elongated catheter shaft 102 having a proximal end and having a distal end and an expandable member 104 located proximate to the distal end of the catheter shaft 102. The expandable member 104 has an outer surface and an inner surface disposed at the distal end portion of the catheter shaft. An inflation lumen 106 can be disposed between the proximal end portion and the distal end portion of the catheter shaft 102. The expandable member 104 is placed in fluid communication with the inflation lumen 106. The inflation lumen can supply fluid under pressure, and establish negative pressure, to the expandable member. The expandable member 104 can thus be inflated and deflated. The elongated catheter is sized and configured for delivery through a tortuous anatomy, and can further include a guidewire lumen 108 that permits it to be delivered over a guidewire 109. The guidewire lumen can have an over-the-wire (OTW) or rapid-exchange (RX) construction, as is well known in the art. Alternatively, the catheter body can include a fixed guidewire to permit the catheter to be delivered to a vessel location without the use of a separate guidewire.

A wide variety of balloon catheters and balloon constructs are known and suitable for use in accordance with the disclosed subject matter. For purpose of illustration and not limitation, the expandable member is fabricated from polymeric material such as compliant, non-compliant or semi-compliant polymeric material or polymeric blends (e.g., a mixture of polymers). For example, the polymers can include one or more thermoplastics and/or thermoset polymers. Examples of thermoplastics include polyolefins; polyamides (e.g., nylon, such as nylon 12, nylon 11, nylon 9, nylon 6, nylon 6/12, nylon 6/11, nylon 6/9, nylon 6/6); polyesters (e.g., polyethylene terephthalate (PET), polybutylene terephthalate (PBT), polyethylene naphthalate (PEN), polytrimethylene terephthalate (PTT)); polyethers; polyurethanes; polyvinyls; polyacrylics; fluoropolymers; copolymers and block copolymers thereof; such as block copolymers of polyether and polyamide (e.g., PEBAX®); and mixtures thereof (e.g., PEBAX® nylon polyether, blends of PEBAX® and nylon). Examples of thermosets include elastomers (e.g., EPDM), epichlorohydrin, polyureas, nitrile butadiene elastomers, and silicones. Other examples of thermosets include epoxies and isocyanates. Biocompatible thermosets can also be used. Biocompatible thermosets include, for example, biodegradable polycaprolactone, poly(dimethylsiloxane) containing polyurethanes and ureas, and polysiloxanes. Ultraviolet curable polymers, such as polyimides, can also be used. Other examples of polymers that can be used to fabricated the expandable member include polyethylenes, polyethylene ionomers, polyethylene copolymers, polyetheretherketone (PEEK), thermoplastic polyester elastomers (e.g., HYTREL®), and combinations thereof. The expandable member can include multiple layers provided, for example, by co-extrusion. Examples of other balloon and catheter embodiments which can be employed in accordance with the disclosed subject matter include U.S. Pat. Nos. 4,748,982; 5,496,346; 5,626,600; 5,300,085, 6,406,457 and application Ser. Nos. 12/371,426; 11/539,944; 12/371,422, each of which is hereby incorporated by reference in their entireties.

The expandable member can be formed using any suitable technique, such as blow molding, film molding, injection molding, and/or extrusion. For example, a polymer tube can be extruded, and can thereafter be stretched and blown to form a balloon. Methods of forming an expandable member from a tube are described, for example, in U.S. Pat. No. 6,120,364 to Laflamme; U.S. Pat. No. 5,714,110 to Wang et al.; and U.S. Pat. No. 4,963,313 to Noddin et al., the disclosures of which are incorporated in their entireties by reference herein.

As embodied herein, the expandable member of the medical device can have a plurality of folds defined therein. For example, a number of conventional balloon catheters include such folds, so as to have a folded configuration and a fully expanded configuration. Generally, the formation of folds can be performed using heat and pressure to form or define creases in the material of the balloon. Examples of such folded balloons are disclosed, for purpose of illustration in U.S. Pat. No. 6,494,906 to Owens; U.S. Pat. No. 6,478,807 to Foreman et al.; and U.S. Pat. No. 5,911,452 to Yan, each of which is hereby incorporated by reference in their entireties.

In accordance with the disclosed subject matter, a plasma treatment with a supply of gas is performed on at least a portion of the outer surface of the expandable member. After the plasma treatment is performed, a therapeutic agent is applied on at least the plasma-treated portion of the outer surface of the expandable member. Plasma treatment for enhanced delivery from the surface of the expandable member can reduce the adhesion of a therapeutic agent to the surface of an expandable member. Details of suitable plasma treatments are provided below.

In accordance with the disclosed subject matter, the expandable member can be in an expanded configuration or in a folded configuration when the plasma treatment is performed thereon. Alternatively, the expandable member in a folded configuration can be inflated with a select amount of inflation medium before performing a plasma treatment. It is preferable that the select amount of inflation medium be sufficient to expose the surfaces of the expandable member desired to be treated by plasma. Particularly, it is beneficial to perform a plasma treatment to a fully inflated expandable member since a fully inflated expandable member provides a larger surface area to which a plasma treatment can be performed, thus allowing for a greater amount and efficacy of plasma treatment.

Figure 3:
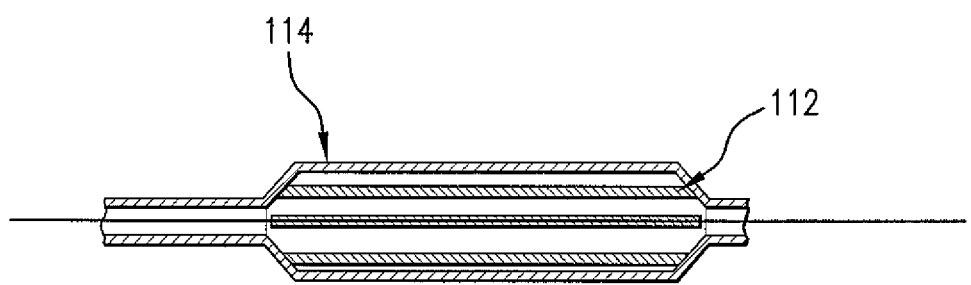
FIG. 3 is a schematic representation of an expandable member with a covering member in accordance with the invention.

Plasma treatment can be performed on the entire exposed surface of the balloon, or only on a portion thereof. In accordance with another aspect of the disclosed subject matter, a plasma treatment is performed on a select portion of an outer surface of an expandable member. For example, and as illustrated in FIG. 3 and in accordance with the disclosed subject matter, a covering member 112 covers the portion(s) of the outer surface of the expandable member 114 where a plasma treatment is not to be performed as desired. The covering member 112 can be removed after the plasma treatment is completed. The term "covering member" used herein, refers to any member or component that can be used to cover the selected surface of an expandable member to prevent or inhibit plasma treatment thereto. A covering member includes, but is not limited to, tapes, shields, tents, wraps, tubes, bags, strips, rings, or any additional applicable covering members. For purpose of illustration and not limitation, the covering member can be made of silicone, polyethylene (PE), low density polyethylene (LDPE), very low density polyethylene (VLDPE), high density polyethylene (HDPE), ultra high molecular weight polyethylene (UHMWPE), poly(tetrafluoroethylene) (PTFE) (also referred as "Teflon®"), fluorinated ethylene propylene (FEP), polyether ether ketone (PEEK), aluminum, stainless steel, or combinations thereof.

Figure 4:
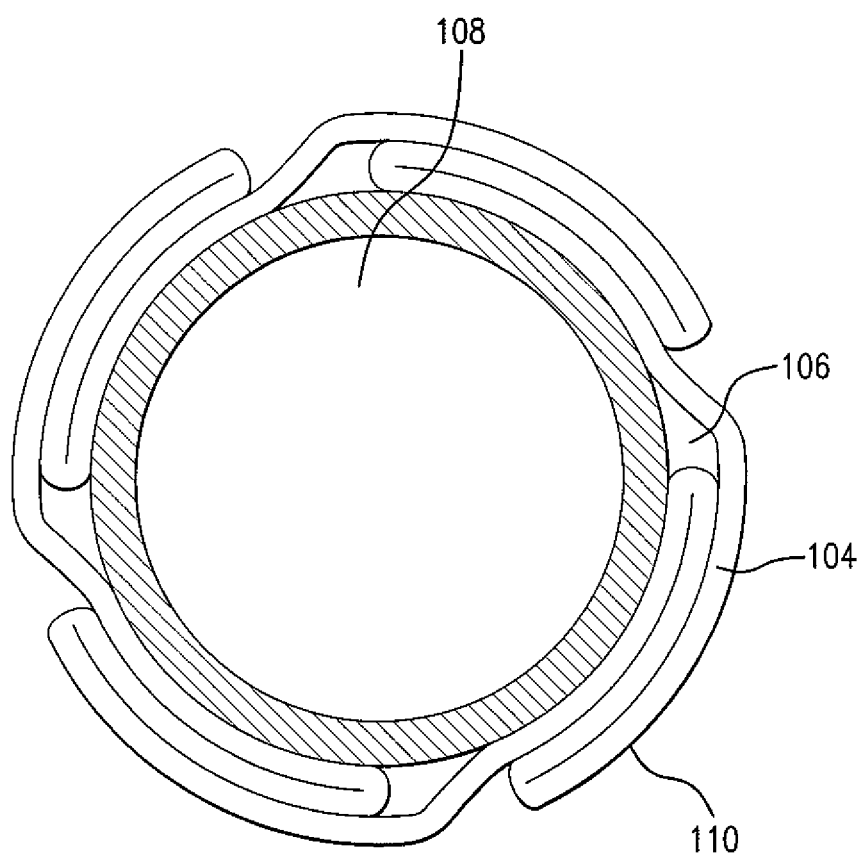
FIG. 4 is a cross-sectional view taken along lines B-B in FIG. 1 after the expandable member is folded in accordance with one embodiment of the invention.

As illustrated in FIG. 4, and in accordance with the disclosed subject matter, the expandable member 104 has at least one therapeutic agent 110 disposed on at least one portion of the outer surface of the expandable member 104. After the plasma treatment, the therapeutic agent 110 can be applied to the outer surface of the expandable member 104 by a variety of techniques, including, but not limited to, direct fluid coating, powder coatings, spraying (air-atomization, ultrasonic, electrostatic, etc.), dip coating, pad printing, transfer by rolling or roll coating, electrografting, jetting, vapor deposition, micro-droplet coating, gravier (slot) coating, or other techniques understood in the art. For example, the dispenser apparatus and corresponding coating techniques disclosed in U.S. Pat. No. 7,455,876 and U.S. Patent Application Publication No. 2010/0055294, the entirety of each is hereby incorporated by reference, can be employed in accordance with the disclosed subject matter. The therapeutic agent 110 can be coated over at least the plasma treated portion or the entirety of the expandable member 104 or medical device in non-uniform or uniform concentrations and/or patterns.

The therapeutic agent coating characteristics can be defined by the therapeutic agent itself, or described further below, as well as by process variables during and after application of the therapeutic agent. For example, for dip-coating process, coating quality and thickness can vary as an effect of variables such as number, rate, and depth of dips along with drying time and temperature. Accordingly, the variables of the particular coating process employed can be controlled to achieve the desired coating characteristics. By way of example, and not limitation, certain coating processes that can be used with the instant invention are described in U.S. Pat. No. 6,669,980 to Hansen; U.S. Pat. No. 7,241,344 to Worsham et al.; and U.S. Publication No. 20040234748 to Stenzel, the disclosures of which are hereby incorporated by reference in their entirety.

Following application of a therapeutic agent to the surface of the expandable member, the expandable member can be folded or alternatively, partially folded, into a low profile configuration. The expandable member can be folded using various techniques well known to those skilled in the art. The folding process can result in an expandable member with several folds, including but not limited to, three, four of five folds. By way of example, and not of limitation, certain exemplary folding processes that can be used in conjunction with the instant invention are described in U.S. Pat. No. 6,988,881 to Motsenbocker et al., which is hereby incorporated by reference in its entirety.

For purposes of illustration, and as embodied herein, the expandable member is deflated to impart a plurality of folds after the plasma treatment is completed, or after the therapeutic agent is applied to the expandable member. Each fold has an outside portion, which is exposed when the expandable member is folded, and an inside portion, which is covered by the outside portion. In one embodiment, the deflated expandable member is folded to align the plasma treated portion(s) of the expandable member to define inside portions of the folds, which are protected during transfer and delivery of the medical device by outside portion(s). By using plasma treatment to reduce adhesion of therapeutic agent to the surface of an expandable member, the applied therapeutic agent has reduced adhesion to the plasma-treated portion(s) of the expandable member. When the medical device is deployed (or expanded) at the target site, plasma treatment renders easier release of therapeutic agent from the plasma-treated portion(s) of the expandable member to the target site.

Various plasma treatments are known and suitable for use in accordance with the disclosed subject matter. For purpose of illustration and not limitation, a plasma treatment is performed by using a low pressure plasma system. In low pressure plasma system, a stable and effective plasma is created by an electromagnetic discharge of a gas at low pressure and low temperature. A plasma is a partially ionized gas containing ions, electrons, atoms, and neutral species. To enable the gas to be ionized in a controlled and qualitative manner, the process is carried out under vacuum conditions. A vacuum vessel is first pumped down via rotary and roots blowers, sometimes in conjunction with high-vacuum pumps, to a generally low vacuum pressure in the range of from about $10^{-2}$ to about $10^{-3}$ mbar. The gas is then introduced into the vessel by means of mass flow controllers and valves. A high-frequency generator, which can be in the kHz, MHz, or microwave range, is then used to ionize the gas into a plasma, forming an environment that has been referred to as "the fourth state of matter" (i.e., in the presence of sufficient energy, a solid can be melted to a liquid, a liquid vaporized into a gas, and a gas ionized into a plasma). The formed reactive particles react in a direct way with the surface without damaging the bulk properties of the treated part.

A low pressure plasma system generally comprises four main components: vacuum system (pump, vessel), energy supply, gas supply, and measurement and control components for the reproducible adjustment of the process parameter. Low pressure plasma treatment is usually a low temperature process, typically from about 40° C. to about 120° C., which can thus avoid thermal damage. The process can induce non-thermally activated surface reactions, causing surface changes, which cannot occur with molecular chemistries at atmospheric pressure. Plasma processing is generally conducted in a controlled environment inside a sealed chamber by the introduction of selected gases. The gas or mixture of gases can be energized by various forms of excitation, for example, alternating current (AC) excitation, direct current (DC) and low-frequency excitation, excitation by means of radio waves or radio frequency (RF), and microwave (MW) excitation. The volatile plasma byproducts are evacuated from the chamber by the vacuum pump, and if necessary can be neutralized in an exhaust scrubber.

Alternatively, or additionally, a plasma treatment is performed by using an atmospheric plasma system which does not require any vacuum equipment. The system allows creation of a uniform and homogeneous high density plasma at atmospheric pressure and low temperatures using a broad range of inert and reactive gases. The atmospheric plasma system treats and functionalizes polymer films in the same way as the vacuum plasma treatment process. In an atmospheric plasma system, plasma is generally generated at atmospheric pressure and low temperatures. An atmospheric plasma may be generated by using an AC or a DC power source, a proprietary designed electrode, a dielectric layer between the electrodes, and an appropriate gas mixture as the plasma medium.

In accordance with the disclosed subject matter, the plasma treatment is performed by supplying a plasma treatment gas to the processing chamber. Many gases or mixture of gases can be used in the invention. For example, the plasma treatment gas includes, but is not limited to, an inert gas, a nitrating gas, or combinations thereof. Suitable inert gases include noble gases, such as argon, neon, xenon, helium, radon, and combinations thereof. A nitrating gas can include nitrogen containing compounds include, but are not limited to, nitrogen, nitrogen oxides, activated-dinitrogen, ammonia, hydrazine, methylhydrazine, dimethylhydrazine, t-butylhydrazine, phenylhydrazine, azoisobutane, ethylazide, tert-butylamine, allylamine, derivatives thereof, and combinations thereof. In addition, the plasma treatment gas can include oxygen, ozone, hydrogen peroxide, carbon dioxide, carbon monoxide, carbon tetrafluoride, water vapor, allyl alcohol, methane, and a combination thereof. The use of these gases and a combination thereof can facilitate plasma formation form a plasma with high density and high uniformity. In one embodiment, the plasma treatment gas is argon. Alternatively, or additionally, the plasma treatment gas is a mixture of argon and oxygen. Oxygen has higher ionization energy than argon, and use of oxygen in addition to argon can result in more uniform plasma than use of argon by itself. The ratio of argon:oxygen supplied at the discharge space is ranged from about 10:90 to about 90:10 by volume. In one embodiment, the ratio of argon:oxygen is about 50:50 by volume. The plasma treatment gas can be supplied at a gas flow rate of from about 0.9 to about 1.2 standard liters per minute (SLPM), such as about 1.08 SLPM.

Power is applied to the processing chamber to generate a plasma. The power application and the plasma generation process can depend upon the process chamber type. An electric field is generated to the gap between two electrodes to ignite a plasma treatment gas introduced into chamber to provide a plasma. A low plasma frequency in a range of from about 10 kHz to about 14 MHz, such as about 40 kHz, can be provided by a low power. A high plasma frequency in a range of from about 1 kHz to about 2,500 MHz, for example, from about 40 KHz to about 14 MHz, can be provided by a high power. Atmospheric plasmas are more easily generated at lower frequencies in the kHz range. A power level of from about 62 to about 720 watts, such as about 380 watts, can be applied to the processing chamber to generate the plasma. The plasma can be generated for from about 40 to about 420 seconds, such as about 75 seconds. The substrate temperature can be maintained at from about 16 to about 100° C., such as from about 25 to about 45° C. The chamber pressure can be maintained at from about 1 to about 2,000 mTorr, such as from about 50 to about 500 mTorr with about 250 mTorr as nominal pressure, during the plasma process. Alternatively or additionally, the plasma can be generated at an atmospheric pressure of from about 680 Torr to about 1,520 Torr, such as from about 720 Torr to about 800 Torr, or about 760 Torr. The substrate can be removed immediately after the plasma treatment or remain in the plasma treatment gas atmosphere for an additional period of time, also referred as "hold time", for example, for about 15 minutes or less. In one embodiment, after the plasma treatment (the power is turned off), the expandable member remains exposed to the plasma treatment gas, argon, at a chamber pressure of about 250 mTorr for about 15 minutes. The "hold time" can quench the free radicals after the plasma treatment is complete, thus preventing oxygenation of the radicals that increases the polarity of the surface of the expandable member.

The effect of plasma treatment depends on a variety of parameters such as the type of plasma (direct current (DC), radio frequency (RF) or microwave (MW)), the discharge power density, the pressure, gas types, and the flow rate of the gas or gas mixture, as well as the treatment time. Thus, the effect of plasma treatment on the adhesion of therapeutic agent to the surface of an expandable member can depend on these plasma treatment parameters as well. For example, depending upon substrate material, coating formulation, and/or plasma conditions, for example, gas types, increasing plasma power and/or treatment time can increase the effect of plasma treatment on the adhesion of therapeutic agent to the surface of an expandable member: reduced adhesion effect. The plasma treatment gas can include oxygen, ozone, hydrogen peroxide, carbon dioxide, carbon monoxide, carbon tetrafluoride, water vapor, allyl alcohol, methane, and a combination thereof. The use of these gases and a combination thereof can facilitate plasma formation and form a plasma with high density and high uniformity. For example, oxygen has lower ionization energy than argon, and use of oxygen in addition to argon as the plasma treatment gas can result in more uniform plasma than use of argon by itself.

The plasma treatment can be performed by various techniques and devices. For purpose of illustration and not limitation, a plasma treatment is performed by a plasma torch, a plasma jet, a plasma stamp, a plasma plume, flame plasma, corona discharge, or ozone treatment. A plasma torch, which is also referred as "plasma arc" or "plasma gun" is a device that generates a directed flow of plasma from its nozzle. A plasma jet generally is operated at atmospheric pressure. A pulsed electric arc is generated by means of high-voltage discharge, for example, from about 5 to about 15 kV, or from about 10 to about 100 kHz, in a plasma jet. A process gas, usually oil-free compressed air flowing past this discharge section, is excited and converted to the plasma state. This plasma then passes through a jet head to arrive on the surface of the material to be treated. A plasma stamp is a device with cavities, which is pressed on the substrate surface. The dimensions of the cavities specify the structure resolution of the plasma treated surface since the plasma burns within these cavities. A flame plasma is formed when a flammable gas and atmospheric air are combined and combusted to form an intense blue flame. Corona discharge is a type of atmospheric plasma developed from an electrode to which is applied a high electrical potential so as to create a plasma around the electrode. Ozone treatment involves formation of ozone and directing the ozone towards a substrate. Ozone is typically created by passing oxygen between two electrodes to which a high voltage is applied to form an arc discharge.

In accordance with the disclosed subject matter, and for purpose of illustration and not limitation, the therapeutic agent or drug can include anti-proliferative, anti-inflammatory, anti-neoplastic, anti-platelet, anti-coagulant, anti-fibrin, anti-thrombotic, anti-mitotic, antibiotic, anti-allergic and antioxidant compounds. Thus, the therapeutic agent can be, again without limitation, a synthetic inorganic or organic compound, a protein, a peptide, a polysaccharides and other sugars, a lipid, DNA and RNA nucleic acid sequences, an antisense oligonucleotide, an antibody, a receptor ligands, an enzyme, an adhesion peptide, a blood clot agent including streptokinase and tissue plasminogen activator, an antigen, a hormone, a growth factor, a ribozyme, and a retroviral vector.

The term "anti-proliferative" as used herein means an agent used to inhibit cell growth, such as chemotherapeutic drugs. Some non-limiting examples of anti-proliferative drugs include taxanes, paclitaxel, and protaxel. Anti-proliferative agents can be anti-mitotic. The term "anti-mitotic" as used herein means an agent used to inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, including, for example, daunorubicin, daunomycin, and plicamycin. Other sub-classes of anti-mitotic agents include anti-mitotic alkylating agents, including, for example, tauromustine, bofumustine, and fotemustine, and anti-mitotic metabolites, including, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing. An example of an anti-mitotic agent includes, but is not limited to, paclitaxel. As used herein, paclitaxel includes the alkaloid itself and naturally occurring forms and derivatives thereof, as well as synthetic and semi-synthetic forms thereof.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, including, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or avb3, antibodies that block binding to gpIIaIIIb or avb3, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

As discussed above, at least one therapeutic agent can be an anti-inflammatory agent. Non-limiting examples of anti-inflammatory agents include prednisone, dexamethasone, hydrocortisone, estradiol, triamcinolone, mometasone, fluticasone, clobetasol, and non-steroidal anti-inflammatories, including, for example, acetaminophen, ibuprofen, naproxen, adalimumab and sulindac. The arachidonate metabolite prostacyclin or prostacyclin analogs is an example of a vasoactive antiproliferative. Other examples of these agents include those that block cytokine activity or inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-MCP1, anti-CCR2, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, including, for example, heparin, heparin sulfate, low molecular weight heparins, including, for example, the compound having the trademark Clivarin®, and synthetic oligosaccharides, including, for example, the compound having the trademark Arixtra®. Also included are direct thrombin inhibitors, including, for example, melagatran, ximelagatran, argatroban, inogatran, and peptidomimetics of binding site of the Phe-Pro-Arg fibrinogen substrate for thrombin. Another class of anti-thrombotic agents that can be delivered is factor VII/IIa inhibitors, including, for example, anti-factor VII/IIa antibodies, rNAPc2, and tissue factor pathway inhibitor (TFPI).

Thrombolytic agents, which can be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Furthermore, the therapeutic agents include a cytostatic agent. The term "cytostatic" as used herein means an agent that mitigates cell proliferation, allows cell migration, and does not induce cell toxicity. These cytostatic agents, include for the purpose of illustration and without limitation, macrolide antibiotics, zotarolimus, everolimus, rapamycin, biolimus, novolimus, myolimus, temsirolimus, deforolimus, structural derivatives and functional analogues of rapamycin, structural derivatives and functional analogues of everolimus, structural derivatives and functional analogues of zotarolimus and any macrolide immunosuppressive drugs. Other therapeutic agents include cytotoxic drugs, including, for example, apoptosis inducers, including TGF, and topoisomerase inhibitors, including, 10-hydroxycamptothecin, irinotecan, and doxorubicin.

Additionally, or alternatively, the therapeutic agent can include other compounds or additives, such as excipients, binding agents, plasticizers, solvents, surfactants, additives, chelators, fillers, and the like. Excipients include, but are not limited to, contrast agents, polysaccharides, amino acids, proteins, non-ionic hydrophilic polymers, ionic hydrophilic polymers, acrylates, hydrophobic polymers, aliphatic polyesters and polyester block copolymers, and, mucoadhesives. Non-ionic hydrophilic polymers include, but are not limited to, polyvinylpyrrolidone (PVP), silk-elastin like polymer, poly(vinyl alcohol), poly(ethylene glycol) (PEG), pluronics (PEO-PPO-PEO), poly(vinyl acetate), poly(ethylene oxide) (PEO), PVP-vinyl acetate (copovidone), polysorbate 80 (Tween 80), and polysorbate 20 (Tween 20). The excipient can also include fatty acids. Further, the excipient can be a lubricious material which improves spreading and uniformity of coating. For example, but not limitation, the plasticizer includes glycerol. In one embodiment, the therapeutic agent includes zotarolimus, PVP, and glycerol. In one embodiment, the zotarolimus:PVP:glycerol weight ratio is about 2:1:0.4.

Additionally if desired and in accordance with the disclosed subject matter, an endoprosthesis, e.g., stent, can be mounted on the expandable member. The type of stent that can be used includes, but is not limited to, bare metal stent, polymeric stent, absorbable stent, drug eluting stent, prohealing stent, self expanding stent, and self-expanding vulnerable plaque implant. The stent coating can contain the same or different therapeutic agents as the catheter or expandable member. Similarly, the coating on the catheter or expandable member can have the same or distinct release kinetics from the therapeutic coating on the stent. For example, it generally is preferable for therapeutic coating to release more readily from the surface of the expandable member than from the surface of the stent.

The coating applied to the expandable member can be allowed to dry prior to placement of the stent thereon. Alternatively, the prosthesis can be mounted on the expandable member fore the coating is allowed to dry or cure past a "tacky" state. This would enable adhesion of the coating on the expandable member to the inside of the prosthesis or stent. This process increases the retention of the prosthesis onto the expandable member (acting as a prosthesis retention enhancer) thus reducing the chance that the stent will move on the expandable member during the torturous delivery through the vascular lumen.

If desired, a protective sheath can be provided to protect the coating during shipping and storage and/or during delivery of the coated expandable member through the body lumen. A variety of sheaths are known, including removable sheaths or balloon covers, retractable sheaths to be withdrawn prior to deployment of the balloon, and elastic sheaths that conform to the balloon upon expansion. Such elastic sheaths are porous or include apertures along a portion thereof. In operation, the inflation of the expandable member causes the sheath to expand for release of the coating and/or therapeutic agent through the porous wall or apertures to the tissue of the arterial wall. For example, see U.S. Pat. No. 5,370,614 to Amundson et al., the disclosure of which is incorporated by reference in its entirety

EXAMPLES

The following examples are presented in order to more fully illustrate certain embodiments of the invention. These examples in no way, however, should be construed as limiting the broad scope of the invention. One skilled in the art can readily devise many variations and modifications of the principles disclosed herein without departing from the scope of the invention.

Figure 5:
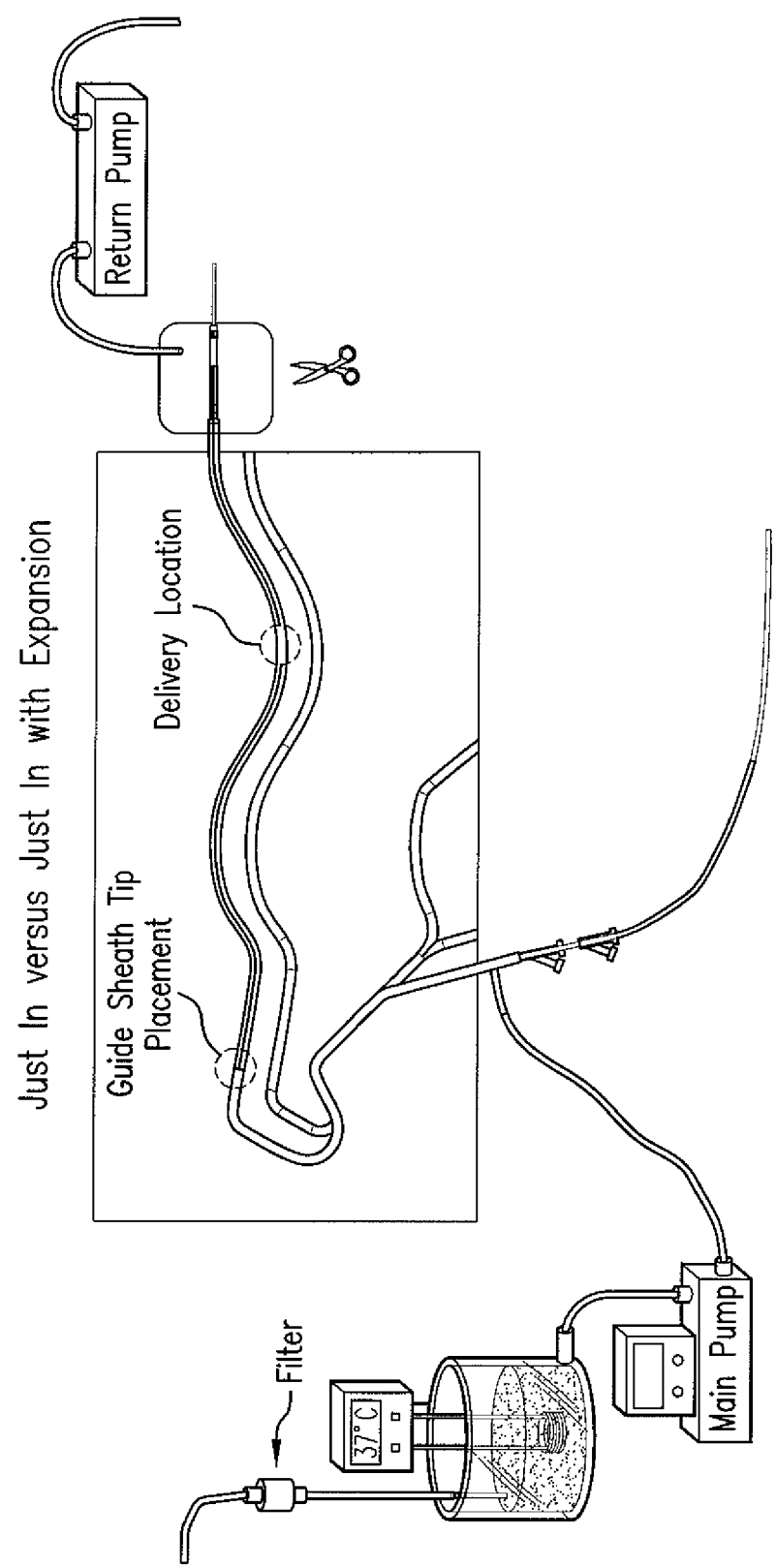
FIG. 5 is a schematic representation of in vitro "Just In" and "Just in With Expansion" assays. Pressure is nominal. Time is 30 seconds. Test Fluid is 6.0 L of 37° C. PBS. The Wall Shear Stress is 0.5 N/m². The flow rate is 650 mL/min. The tubing is 6.0 mm ID Tecoflex.

With reference to the following examples, a method of testing the coating adhesion to a balloon is described herewith. Directly testing the adhesion of the coating to the balloon can be difficult. The coating itself tends to have poor tensile properties, and it is important to determine the adhesion of the coating when wet. Wet adhesion generally is an indicator of how well the coating will stay on the balloon during delivery and during expansion. Two in vitro assays, "Just In" assay and "Just in With Expansion" assay were developed to measure the wet adhesion of a weak coating on a flexible substrate. These assays simulate the loss of coating from a device while it is passed through a synthetic vasculature model. A diagram of the two in vitro assays is shown in FIG. 5. For purpose of these examples, the expandable member is a drug coated balloon.

Under the "Just In" assay, the drug-coated balloon is advanced through the hemostatic valve, guide sheath, and simulated vasculature to the delivery location as desired. The balloon device is held at the delivery location for about 30 seconds and then advanced clear of the model to where the balloon is cut off from the catheter. Under the "Just In" assay, the drug-coated balloon is delivered to the target site but not inflated, and thus the drug remaining on the balloon after the test represents the potential drug amount for treatment. A higher result from "Just In" test represents more drug amount available for treatment.

Under the "Just in With Expansion" assay, a drug-coated balloon is advanced to the delivery location as desired, expanded to nominal pressure, held for about 30 seconds, deflated, and then advanced clear of the model to where the expandable member is cut off from the catheter. Under the "Just in With Expansion" assay, the balloon is delivered to the target site and inflated, and thus the drug remaining on the balloon after the test estimates how much drug is remaining on the balloon after treatment. A lower result from "Just in With Expansion" test indicates that more drug amount is released from the balloon to the target site. The drug remaining on the balloon after both tests is assayed by high performance liquid chromatography (HPLC).

Example 1

A group of Fox SV nylon-12 balloons sold by Abbott Vascular were tested in this study. The study had three arms. A plasma treatment with a supply of argon at a power of 700 watts (also referred as "high power argon plasma") was performed for 420 seconds on the balloons in Arm 1. A plasma treatment with a supply of argon at a power of 62 watts (also referred as "low power argon plasma") was performed for 75 seconds on the balloons in Arm 2. No plasma treatment was performed on the balloons in Arm 3. A 300 $\mu g/cm^2$ dose of zotarolimus/poly(N-vinyl pyrrolidone)(PVP)/glycerol (ZPG) formulation with a weight ratio of 2:1:0.4 was applied to the balloons after the plasma treatment. After re-folding, sheathing and e-beam sterilization, these balloons coated with ZPG formulation were tested with the in vitro "Just In" and "Just in With expansion" assays as shown in FIG. 5.

Figure 6:
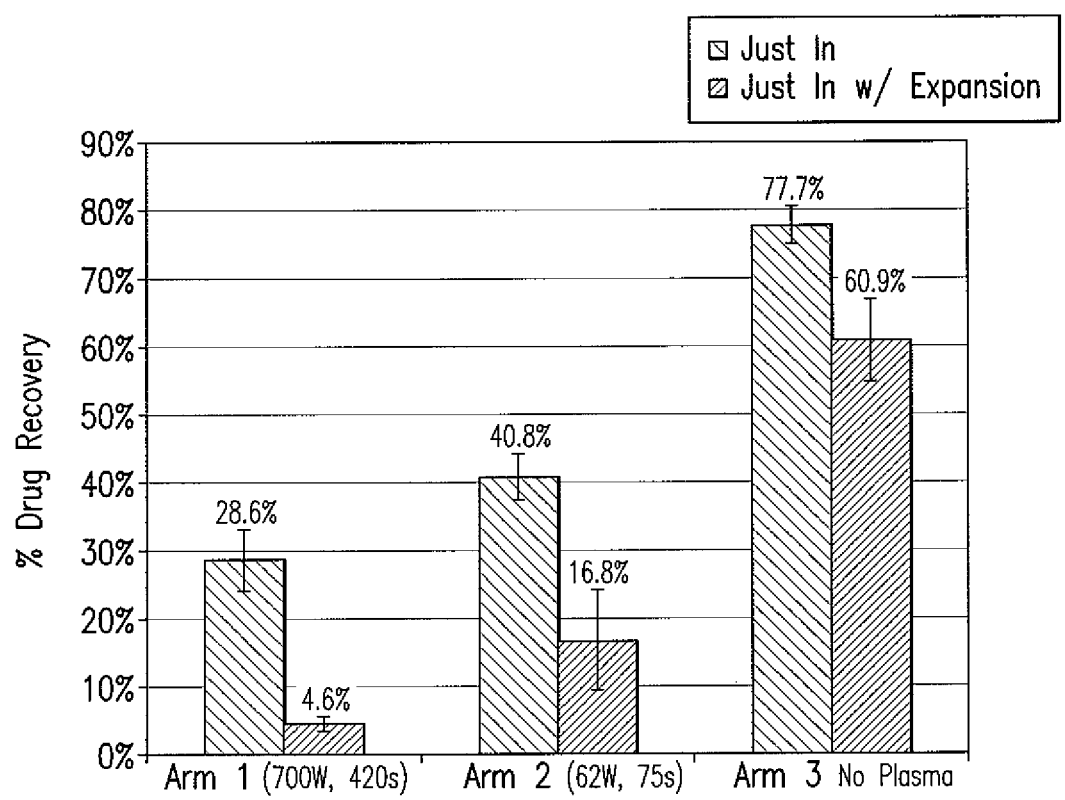
FIG. 6 is graphical representation of results from in vitro "Just In" and "Just in With Expansion" assays from Example 1.

The results, e.g., drug recovery percentage, from the in vitro "Just In" and "Just in With Expansion" assays for the three arm studies are shown in FIG. 6. Under "Just In" assay as shown in FIG. 6, drug recovery percentage for Arm 1 is about 28.6%, drug recovery percentage for Arm 2 is about 40.8%, and drug recovery percentage for Arm 3 is about 77.7%. Under "Just in With Expansion" assay as shown in FIG. 6, drug recovery percentage for Arm 1 is about 4.6%, drug recovery percentage for Arm 2 is about 16.8%, and drug recovery percentage for Arm 3 is about 60.9%. The results revealed that both the high and low power argon plasma treatments lowered the coating adhesion to the balloons compared with no plasma treatment, e.g., lower drug recovery percentage in both "Just In" and "Just in With Expansion" assays. These findings were opposite to conventional thinking, as plasma treatment is often used to modify surfaces in order to improve adhesion. In both assays, less drug coating remained on the balloon for the plasma treatment systems (Arm 1 and Arm 2) compared to the no plasma treatment control (Arm 3). As the coating formulation was the same in all arm studies, this result could not be attributed to a difference in dissolution of the coating but must be due to difference in the coating adhesion. Moreover, since drug recoveries of Arm 1 and Arm 2 systems were statistically different in both tests, it was observed that with increasing plasma power and time the coating adhesion was weaker or lower.

Ideally, it would be preferred that no drug is released during delivery to the lesion and all drug would be released during inflation and transfer to the tissue minimizing systemic drug delivery. Therefore, drug recovery ideally would be close to 100% after "Just In" and close to 0% after "Just in With Expansion." A "theoretical amount of drug delivered/released" is calculated by subtracting the drug recovery for "Just in With Expansion" from "Just In." The "theoretical drug released" for these three arm studies are shown in Table 1. The no plasma treatment group (Arm 3) showed the least drug "delivered" and the two plasma treatment groups (Arm 1 and Arm 2) showed more drug "delivered." The amount of drug "delivered" is the same in Arm 1 and Arm 2.

TABLE 1

| Balloon treatment | Drug "delivered" | Drug "delivered" |
|---|---|---|
| Arm 1 (Plasma Recipe 5) | 540 ± 105 μg | 24.4 ± 4.7% |
| Arm 2 (Plasma Recipe 2) | 532 ± 180 μg | 24.0 ± 8.1% |
| Arm 3 (No plasma treatment) | 361 ± 139 μg | 16.3 ± 6.3% |

Teflon blocks were used to support the devices in the plasma treatment reactor chamber. One explanation for the observed increased drug loss with plasma treatment is that Teflon (material from the block holding the device) is being sputtered onto the balloon during the plasma treatment cycle. Another explanation is that the argon plasma is making the surface of the balloon more polar, which can cause the glycerol to migrate to the surface of the balloon, thus creating a weak boundary layer for the coating.

Example 2

This present study was carried out to determine the main effects of plasma treatment variables on drug coating adhesion to the balloon, in particular, to determine the effect of several plasma treatment parameters on the adhesion of the ZPG formulation coating to the Fox SV balloon. A group of Fox SV nylon-12 balloons were tested in this study. A 300 μg/cm$^2$ dose of ZPG formulation with a weight ratio of 2:1:0.4 were directly coated on the Fox SV nylon-12 balloons after plasma treatment with various plasma treatment parameters described below.

The control factors in this study are described in Table 2. All devices were treated with plasma using poly(etheretherketone) PEEK blocks to support the catheters in the chamber. In Table 1, "Power" represents the power of the plasma treatment cycle in watts; "Time" represents duration of the plasma treatment cycle in seconds; and "Gas Type" represents working gas of the plasma treatment. In addition, "Argon-no hold" describes a plasma treatment with a supply of argon where the chamber immediately vents to atmospheric oxygen and pressure immediately after the plasma treatment cycle is complete. Argon plasma creates free radicals on the balloon surface. When the chamber is opened, the free radials can react with oxygen to oxygenate the surface and make it more polar. "Argon-hold" describes a plasma treatment with a supply of argon and the device is held in an argon rich environment for a "hold time" after the plasma treatment cycle is complete before opening to atmosphere. During this "hold time," the samples were exposed to argon at about 250 mTorr for 15 minutes at zero power. This "hold time" can quench the free radicals after the plasma treatment cycle is complete, thus preventing oxygenation of the radicals that increase the polarity of the balloon surface. "Oxygen/Argon" describes a plasma treatment with a supply of a mixture of argon and oxygen. Oxygen has higher ionization energy than argon and a mixture of oxygen and argon can result in a more uniform plasma across the chamber.

TABLE 2

| | Plasma Control Factors | | | |
|---|---|---|---|---|
| No. | Control Factor | Low (−) | Center Point | High (+) |
| 1 | Power (Watts) | 62 | 381 | 700 |
| 2 | Time (seconds) | 40 | 230 | 420 |
| 3 | Gas Type | Argon-no hold | Argon-hold | Oxygen/Argon (50/50) |

Full factorial and one center point for each of the three tests (45 total samples) are described in Table 3. These 15 conditions were manufactured three times each in order to fulfill three different tests: 15 trials for Baseline TC, which represents the drug amount on the drug-coated balloon prior to the "Just-In" or "Just-In-with Expansion" essays, 15 trials for "Just In" assay, and 15 trials for "Just in With Expansion" assay. The quantity of drug on the balloons as made is referred to as the Baseline Total Content (Baseline TC).

TABLE 3

| | Table of plasma treatment conditions | | | |
|---|---|---|---|---|
| Arm | Power (Watts) | Time (Seconds) | Gas Type | Sample Size |
| A1 | 62 | 40 | Argon-no hold | 1 |
| A2 | 62 | 420 | Argon-no hold | 1 |
| A3 | 381 | 230 | Argon-no hold | 1 |
| A4 | 700 | 40 | Argon-no hold | 1 |
| A5 | 700 | 420 | Argon-no hold | 1 |
| B1 | 62 | 40 | Argon | 1 |
| B2 | 62 | 420 | Argon | 1 |
| B3 | 381 | 230 | Argon | 1 |
| B4 | 700 | 40 | Argon | 1 |
| B5 | 700 | 420 | Argon | 1 |
| C1 | 62 | 40 | Oxygen/Argon (50/50) | 1 |
| C2 | 62 | 420 | Oxygen/Argon (50/50) | 1 |
| C3 | 381 | 230 | Oxygen/Argon (50/50) | 1 |
| C4 | 700 | 40 | Oxygen/Argon (50/50) | 1 |
| C5 | 700 | 420 | Oxygen/Argon (50/50) | 1 |
| D (No plasma) | N/A | N/A | N/A | 5 |

The plasma treatment parameters used for each gas type are shown in Table 4.

TABLE 4

| Gas type | % Argon | % Oxygen | Control Mode | Temperature (° C.) | Blower Speed % | Flow Rate (SLM) | Hold Time (min) | Expected Pressure Range (mTorr) |
|---|---|---|---|---|---|---|---|---|
| Argon-no hold | 100 | 0 | Fixed Flow | 25 | 100 | 1.08 | 0 | 230-320 |
| Argon-hold | 100 | 0 | Fixed Flow | 25 | 100 | 1.08 | 15 | 230-320 |
| Oxygen/Argon | 50 | 50 | Fixed Flow | 25 | 85 | 1.08 | 0 | 230-320 |

In addition, this study also included coating of a control arm (no plasma treatment) as well as coating of two other arms to compare the effect of using a Teflon block versus a PEEK block to hold the devices during the plasma cycle, as shown in Table 5. All units were folded and sheathed after coating and were e-beam sterilized before testing.

TABLE 5

Summary of study arms

| ZPG (5% zot 85/15 with 2/1/0.4) | Arm | Baseline TC | Just In | Just In with Expansion | Extra (2 per plasma recipe) | Total |
|---|---|---|---|---|---|---|
| Argon-hold (PEEK block, plasma recipe 1-5) | A1-A5 | 5 | 5 | 5 | 10 | 25 |
| Argon-no hold (PEEK block, plasma recipe 1-5) | B1-B5 | 5 | 5 | 5 | 10 | 25 |
| Oxygen/Argon (PEEK block, plasma recipe 1-5) | C1-C5 | 5 | 5 | 5 | 10 | 25 |
| Control units and Teflon vs. PEEK side experiment | | | | | | |
| No plasma | D | 5 | 5 | 5 | 2 | 17 |
| Argon-hold (P-700 w, t = 420 s, Teflon block) | E | 0 | 5 | 5 | 2 | 12 |
| Argon-no hold (P-700 w, t = 420 s, Teflon block) | F | 0 | 5 | 5 | 2 | 12 |

Figure 7:
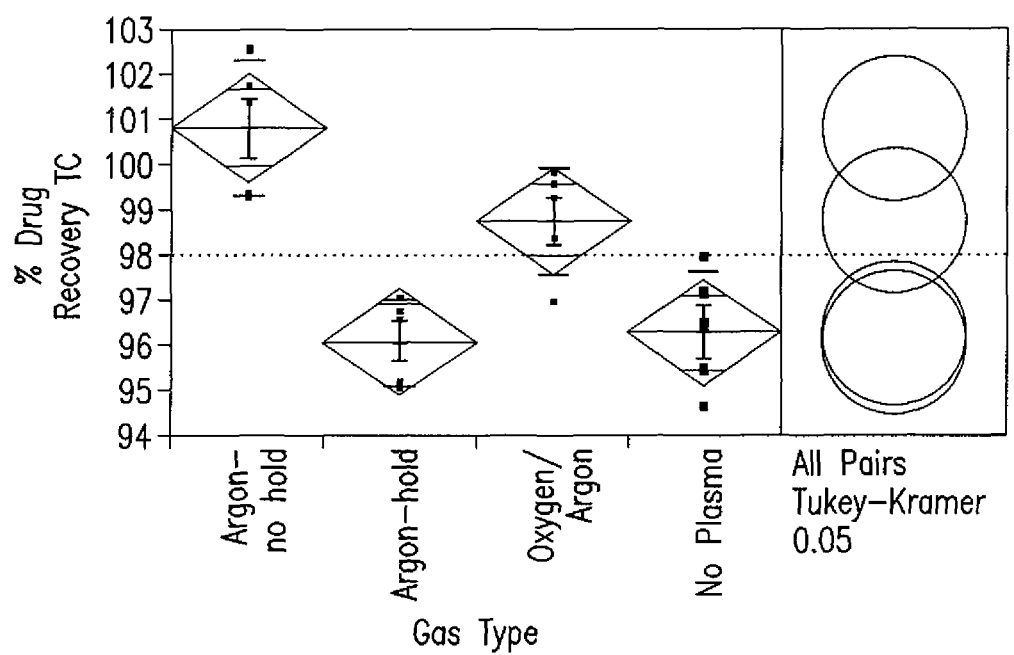
FIG. 7 is a graphical representation of the results for Baseline Total Content (TC) from Example 2.

The results for Baseline TC are shown in FIG. 7. More drug coating remained on the balloons for argon-no hold and oxygen/argon plasma treatment systems than for argon-hold plasma treatment system and no plasma treatment control. For Baseline TC, there was no difference within each group of gas types, and power and time did not affect Baseline TC results. Table 6 below provides the statistical data from FIG. 7. This shows that gong into the "Just In" and "Just In with Expansion" assays, the drug content of the various arms were equivalent.

TABLE 6

| Summary of Fit | |
|---|---|
| RSquare | 0.753627 |
| Adj Rsquare | 0.707432 |
| Root mean square error | 1.242276 |
| Mean of response | 97.97 |
| Observations (or sum wgts) | 20 |

| Level | Mean |
|---|---|
| Argon-no hold A | 100.80000 |
| Oxygen/Argon A | 98.74000 |
| No Plasma B | 96.28000 |
| Argon-hold B | 96.06000 |
| Levels not connected by same letter are significantly different | |

Figures 8A, 8B:
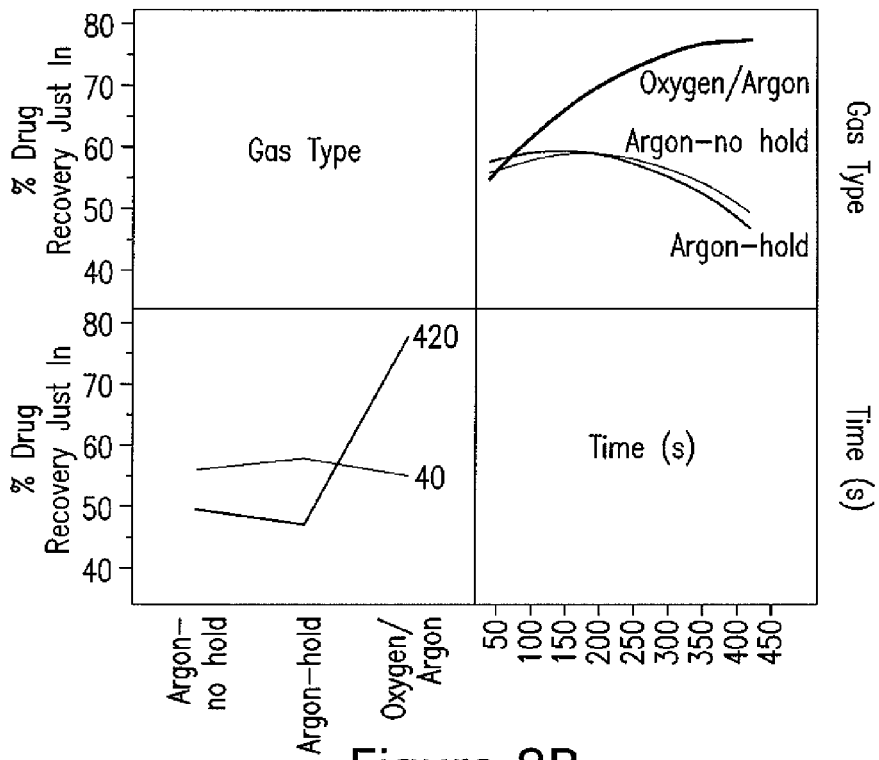
FIGS. 8A-B are graphical representations of results from in vitro "Just In" assay from Example 2.

The results from the in vitro "Just In" test are shown in FIGS. 8A-8B. Time factor for oxygen/argon was significant and increased time for plasma treatment resulted in increase drug recovery for "Just In" test (±11% from the mean), see FIG. 8B. Time factor for argon-no hold and argon-hold were not significant, but increased time for plasma treatment with oxygen/argon trended toward decreased drug recovery, see FIG. 8B. Power had very little to no effect on any gas type for "Just In" results.

The results from in vitro "Just in With Expansion" tests are shown in FIG. 9. Power, time and power combined with time did not show significant main effects for each gas type for "Just In with Expansion" results.

Figure 10:
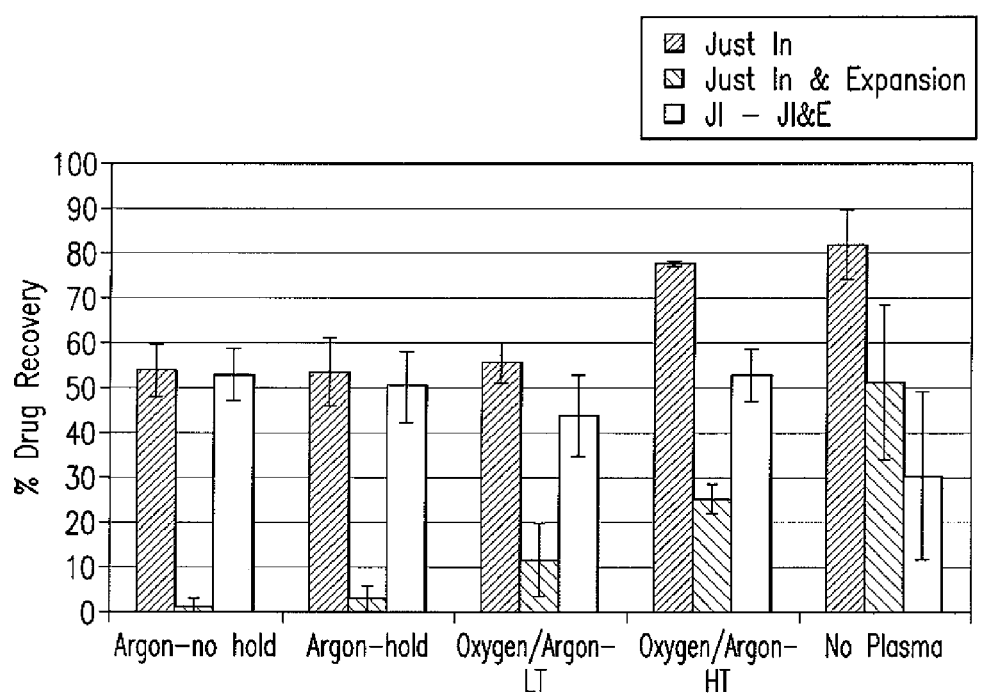
FIG. 10 is a graphical representation of results from in vitro "Just In" and "Just in With Expansion" assays from Example 2.

Overall results for all gas types and no plasma treatment control groups from in vitro "Just In" and "Just in With Expansion" are shown in FIG. 10. The results showed that there was no main effect of power or time for argon-no hold and argon-hold plasma treatment groups. The effect of plasma power and/or treatment time on plasma treatment and further on the adhesion of therapeutic agent to the surface of an expandable member depends upon various parameters, for example, substrate material, coating formulation, and various plasma conditions, e.g., gas types. Given the significance of time for oxygen/argon plasma treatment, the data points were separated into two groups: high time (HT) and low time (LT), see FIG. 10. The results showed that time is a main factor for oxygen/argon plasma treatment and it can be used to "tune" amount of drug released.

Example 3

Figure 11:
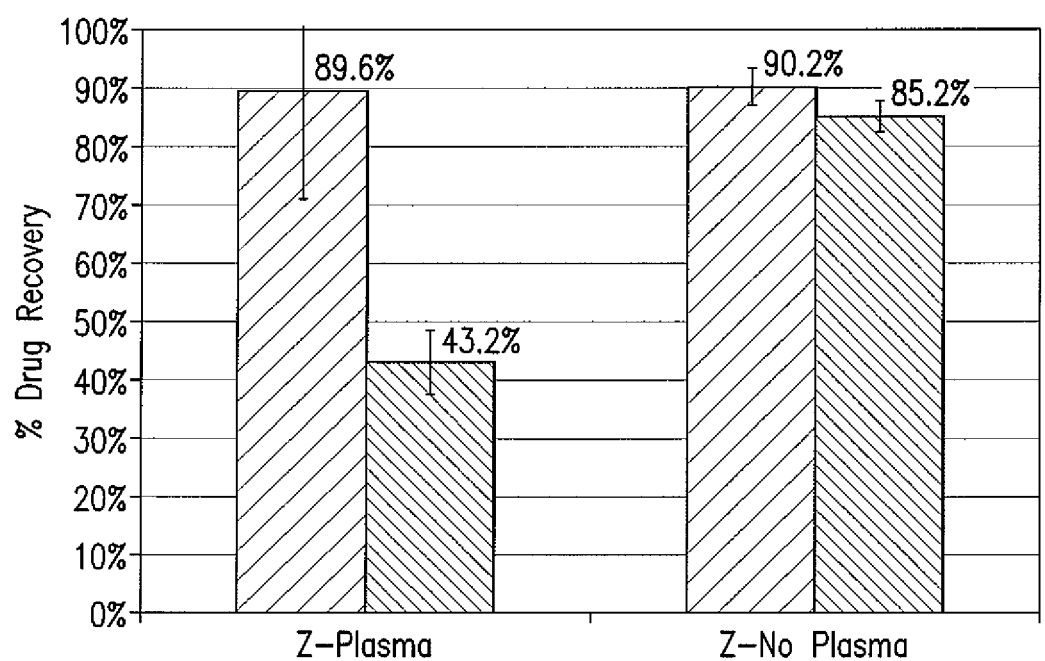
FIG. 11 is a graphical representation of results from in vitro "Just In" and "Just In with Expansion" assays from Example 3.

This present study was performed to test the effect of plasma treatment on pure zotarolimus adhesion to Agiltrac balloons. The Agiltrac balloon is a second-generation 0.035" guide-wire-compatible balloon. A plasma treatment with a supply of argon at a power of 700 watts (also referred as "high power argon plasma") was performed for 420 seconds on Agiltrac® balloons. Six Agiltrac® balloons were used for control without plasma treatment. After the plasma treatment, a 300 µg/cm² dose of pure zotarolimus formulation was directly applied to the balloons. After re-folding, sheathing and e-beam sterilization, these Agiltrac® balloons coated with pure zotarolimus formulation were tested with the in vitro "Just In" and "Just in With expansion" assays, as shown in FIG. 5. The results from in vitro "Just In" and "Just in With Expansion" assays are shown in FIG. 11. The effect of the argon gas plasma treatment on the adhesion of the pure zotarolimus formulation was pronounced. On an Agiltrac® balloon, which has only been cleaned by sonication in isopropyl alcohol (IPA), the zotarolimus coating shows strong adhesion to the balloon, perhaps too high such that drug is not released. The no plasma treatment group was only cleaned by sonication in 100% IPA (as all balloons are cleaned by sonication in IPA prior to coating), and the hydrophobic zotarolimus stayed on the balloon after "Just In with Expansion" test so well (85.2% drug recovery) that its effectiveness as a drug-coated balloon delivery would be questionable. After an argon plasma treatment (power=700 w, time=420 s), the zotarolimus coating adhesion was reduced. The difference between the "Just In" and "Just In with Expansion" tests provides a theoretical drug delivery of 46.4%.

Example 4

Figure 12A:
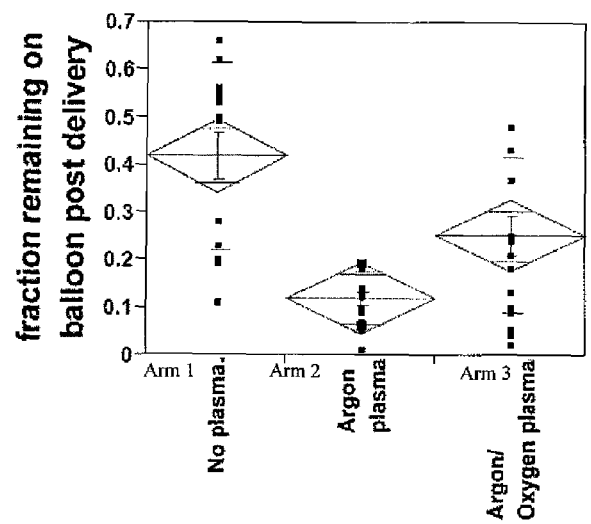
FIGS. 12A-B are graphical representations of drug recovery post delivery from Example 4.
Figure 12B:
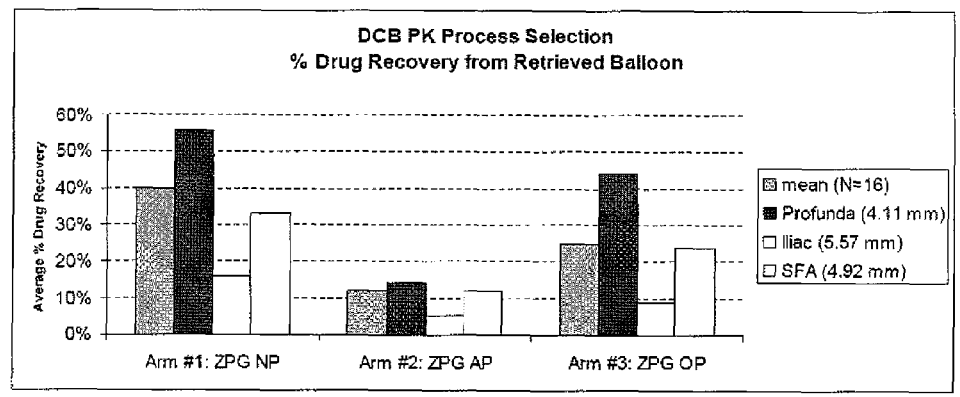

This present study is provided to test the effect of plasma treatment on the in vivo performance of Fox SV balloons in healthy porcine iliofemoral. A group of Fox SV balloons were provided. The study had three arms. No plasma treatment was performed on the balloons in Arm 1. A plasma treatment with a supply of argon at a power of 700 watts was performed for 420 seconds with no "hold time" on the balloons in Arm 2. A plasma treatment with a supply of oxygen/argon (50:50) at a power of 700 watts was performed for 420 seconds with no "hold time" on the balloons in Arm 3. A 300 µg/cm² dose of ZPG formulation with a weight ratio of 2:1:0.4 was applied to the balloons in these balloons after the plasma treatment. All units were folded and sheathed after coating and were e-beam sterilized before testing. The fractions of zotarolimus remaining on the Fox SV balloons post-delivery are less for the balloons in Arm 2 (argon plasma treatment) than those in Arm 3 (oxygen/argon plasma treatment) which is less than the balloons in Arm 1 (no plasma treatment), as shown in FIGS. 12A-B. In addition, drug delivery from balloons in Arm 1 (no plasma treatment) was more responsive to delivery parameters, e.g., inflation pressure, vessel size, and balloon artery ratio, etc., than the balloons with plasma treatment, and the drug delivery from the balloons in Arm 2 (argon plasma treatment) showed to be the least responsive.

While the disclosed subject matter is described herein in terms of certain preferred or exemplary embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method of coating a balloon comprising:
   selecting a therapeutic agent, wherein the therapeutic agent is a cytostatic agent;
   providing a balloon having an outer surface having a surface adhesion characteristic relative to the therapeutic agent;
   performing a plasma treatment with a supply of gas comprising argon on at least a portion of the outer surface of the balloon to reduce the surface adhesion characteristic of the outer surface relative to the therapeutic agent; and
   applying the therapeutic agent directly onto at least the plasma treated portion of the outer surface of the balloon after performing the plasma treatment.

2. The method of claim 1, wherein performing the plasma treatment is by using a negative pressure plasma system.

3. The method of claim 2, wherein the negative pressure plasma system comprises a vacuum system.

4. The method of claim 1, wherein performing the plasma treatment is by using an atmospheric plasma system.

5. The method of claim 1, wherein performing plasma treatment is by a plasma jet, a plasma stamp, a plasma plume, a plasma torch, flame plasma, corona discharge, or ozone treatment.

6. The method of claim 1, wherein the plasma treatment is performed within a plasma reactor chamber.

7. The method of claim 1, wherein the gas is argon.

8. The method of claim 1, wherein the gas further comprises oxygen, ozone, hydrogen peroxide, carbon dioxide, carbon monoxide, carbon tetrafluoride, hydrogen, nitrogen, water vapor, nitrogen oxides, ammonia, allyl amine, allyl alcohol, methane, or a combination thereof.

9. The method of claim 8, wherein the gas is a mixture of argon and oxygen.

10. The method of claim 9, wherein the ratio of argon:oxygen is from about 10:90 to about 90:10 by volume.

11. The method of claim 9, wherein the ratio of argon:oxygen is about 50:50 by volume.

12. The method of claim 1, wherein the plasma treatment is performed at a plasma frequency of from about 1 kHz to about 2,500 MHz.

13. The method of claim 1, wherein the plasma treatment is performed at a plasma frequency of from about 10 kHz to about 14 MHz.

14. The method of claim 1, wherein the plasma treatment is performed at a plasma frequency of from about 40 kHz to about 14 MHz.

15. The method of claim 1, wherein the plasma treatment is performed at a power of from about 62 watts to about 700 watts.

16. The method of claim 1, wherein the plasma treatment is performed at a power of about 380 watts.

17. The method of claim 1, wherein the plasma treatment is performed at a gas flow rate of from about 0.9 standard liters per minute to about 1.2 standard liters per minute.

18. The method of claim 1, wherein the plasma treatment is performed at a gas flow rate of about 1.08 standard liters per minute.

19. The method of claim 1, wherein the plasma treatment is performed at a pressure of from about 1 mTorr to about 2,000 mTorr.

20. The method of claim 1, wherein the plasma treatment is performed at a pressure of from about 50 mTorr to about 500 mTorr.

21. The method of claim 1, wherein the plasma treatment is performed at a pressure of from about 680 Torr to about 1,520 Torr.

22. The method of claim 1, wherein the plasma treatment is performed at a pressure of from about 720 Torr to about 800 Torr.

23. The method of claim 1, wherein the plasma treatment is performed at a pressure of about 760 Torr.

24. The method of claim 1, wherein the plasma treatment is performed at a temperature of from about 16 degrees Celsius to about 100 degrees Celsius.

25. The method of claim 1, wherein the plasma treatment is performed at a temperature of from about 25 degrees Celsius to about 45 degrees Celsius.

26. The method of claim 1, wherein the balloon is exposed to the plasma treatment for about 10 seconds to about 1,000 seconds.

27. The method of claim 1, wherein the balloon is exposed to the plasma treatment for about 40 seconds to about 420 seconds.

28. The method of claim 1, wherein the balloon is exposed to the plasma treatment for at least about 75 seconds.

29. The method of claim 1, wherein the balloon is further exposed to the gas for about 15 minutes or less after the plasma treatment is completed.

30. The method of claim 1, wherein applying the therapeutic agent on at least the plasma treated portion of the outer surface of the balloon includes spraying, dipping, syringe coating, electrospinning, electrostatic coating, direct coating, or a combination thereof.

31. The method of claim 1, wherein the therapeutic agent is selected from the group consisting of zotarolimus, everolimus, rapamycin, biolimus, myolimus, novolimus, deforolimus, temsirolimus, derivatives and analogues thereof, and a combination thereof.

32. The method of claim 1, wherein the therapeutic agent further comprises at least one compound selected from the group consisting of excipients, binding agents, plasticizers, solvents, surfactants, additives, chelators, and fillers.

33. The method of claim 32, wherein the excipient is selected from the group consisting of contrast agents, polysaccharides, amino acids, proteins, non-ionic hydrophilic polymers, ionic hydrophilic polymers, acrylates, hydrophobic polymers, aliphatic polyesters and polyester block copolymers, and mucoadhesives.

34. The method of claim 32, wherein the excipient is polyvinylpyrrolidone.

35. The method of claim 32, wherein the plasticizer is glycerol.

36. The method of claim 1, wherein the balloon is composed of nylon 12, nylon 11, nylon 9, nylon 6, nylon 6/12, nylon 6/11, nylon 6/9, nylon 6/6, polyether block amide nylon copolymer, blends of polyether block amide and nylon, thermoplastic polyester elastomer, or polyethylene.

37. The method of claim 1, wherein performing the plasma treatment comprises:
covering a select portion of the outer surface of the balloon with a covering member;
performing the plasma treatment with the supply of gas comprising argon on the outer surface of the balloon partially covered by the covering member; and
removing the covering member after performing the plasma treatment.

38. The method of claim 37, wherein the covering member is made of silicone, polyethylene (PE), low density polyethylene (LDPE), very low density polyethylene (VLDPE), high density polyethylene (HDPE), ultra high molecular weight polyethylene (UHMWPE), poly(tetrafluoroethylene) (PTFE), fluorinated ethylene propylene (FEP), polyether ether ketone (PEEK), aluminum, stainless steel, or combinations thereof.

39. The method of claim 1, wherein the balloon is in a folded configuration.

40. The method of claim 1, wherein the balloon is in an expanded configuration.

41. The method of claim 40, further comprising inflating the balloon with an amount of inflation medium sufficient to expose the surfaces of the balloon to be plasma treated before performing the plasma treatment.

42. The method of claim 41, further comprising deflating the balloon to impart a plurality of folds therein after performing the plasma treatment, the fold having an inside portion and an outside portion.

43. The method of claim 42, further comprising folding the balloon after deflating the balloon, resulting in the plasma treated portions of the balloon being the inside portions of the folds.

* * * * *